(12) United States Patent
Zafar et al.

(10) Patent No.: US 11,510,598 B2
(45) Date of Patent: Nov. 29, 2022

(54) PH SENSITIVE SURGICAL TOOL

(71) Applicant: INTERNATIONAL BUSINESS MACHINES CORPORATION, Armonk, NY (US)

(72) Inventors: Azeem Zafar, Smyrna, GA (US); Sufi Zafar, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 468 days.

(21) Appl. No.: 16/691,740

(22) Filed: Nov. 22, 2019

(65) Prior Publication Data
US 2020/0085353 A1    Mar. 19, 2020

Related U.S. Application Data

(62) Division of application No. 15/458,223, filed on Mar. 14, 2017, now Pat. No. 10,952,654.

(51) Int. Cl.
| | |
|---|---|
| *A61B 5/145* | (2006.01) |
| *A61B 5/00* | (2006.01) |
| *A61B 5/1468* | (2006.01) |
| *A61B 5/1495* | (2006.01) |

(52) U.S. Cl.
CPC ........ *A61B 5/14539* (2013.01); *A61B 5/1468* (2013.01); *A61B 5/1495* (2013.01); *A61B 5/742* (2013.01)

(58) Field of Classification Search
CPC ............ A61B 5/14865; A61B 5/14514; A61B 5/14532; A61B 5/14546
See application file for complete search history.

(56) References Cited

U.S. PATENT DOCUMENTS

| | | | |
|---|---|---|---|
| 371,078 A | 10/1887 | Lanahan | |
| 3,467,582 A | 9/1969 | Kokholm | |
| 4,403,984 A | 9/1983 | Ash et al. | |
| 4,535,773 A | 8/1985 | Yoon | |
| 4,625,171 A | 11/1986 | Sekihara et al. | |
| 4,689,567 A | 8/1987 | Maudsley | |

(Continued)

OTHER PUBLICATIONS

Kato, Yasumasa, et al., "Acidic Extracellular Microenvironment and Cancer." Cancer Cell International, vol. 13, No. 1, 2013, p. 89 (Year: 2013).

(Continued)

*Primary Examiner* — Christian Jang
(74) *Attorney, Agent, or Firm* — Cantor Colburn LLP; Kristofer Haggerty

(57) ABSTRACT

Embodiments include methods, systems, and apparatus for identification, detection, and removal of cancerous cells from a patient. The apparatus includes an apparatus handle. The apparatus also includes a display including a pH measurement result. The apparatus also includes an apparatus tip including a reference electrode and a plurality of sensing surfaces, wherein each of the plurality of sensing surfaces is connected to a base of a bipolar junction transistor (BJT) device. The BJT device further includes a collector and an emitter. The apparatus also includes automation circuitry including a processing unit in communication with the apparatus tip and the display. The plurality of sensing surfaces includes a conducting material.

8 Claims, 11 Drawing Sheets

(56) References Cited

U.S. PATENT DOCUMENTS

| | | |
|---|---|---|
| 4,751,464 A | 6/1988 | Bridges |
| 5,046,497 A | 9/1991 | Millar |
| 5,060,658 A | 10/1991 | Dejter, Jr. et al. |
| 5,209,721 A | 5/1993 | Wilk et al. |
| 5,291,607 A | 3/1994 | Ristic et al. |
| 5,320,101 A | 6/1994 | Faupel et al. |
| 5,383,465 A | 1/1995 | Lesny et al. |
| 5,431,628 A | 7/1995 | Millar |
| 5,442,290 A | 8/1995 | Crooks |
| 5,520,189 A | 5/1996 | Malinowski et al. |
| 5,634,464 A | 6/1997 | Jang et al. |
| 5,735,278 A | 4/1998 | Hoult et al. |
| 5,758,646 A | 6/1998 | Van Der Meulen et al. |
| 5,893,881 A | 4/1999 | Elsberry et al. |
| 6,108,439 A | 8/2000 | Ishiguro |
| 6,109,270 A | 8/2000 | Mah et al. |
| 6,245,026 B1 | 6/2001 | Campbell et al. |
| 6,256,533 B1 | 7/2001 | Yuzhakov et al. |
| 6,309,370 B1 | 10/2001 | Haim et al. |
| 6,397,095 B1 | 5/2002 | Eyuboglu et al. |
| 6,564,087 B1 | 5/2003 | Pitris et al. |
| 6,592,519 B1 | 7/2003 | Martinez |
| 6,612,190 B2 | 9/2003 | Takeuchi et al. |
| 6,626,899 B2 | 9/2003 | Houser et al. |
| 6,629,343 B1 | 10/2003 | Chesney et al. |
| 6,692,494 B1 | 2/2004 | Cooper et al. |
| 6,733,459 B1 | 5/2004 | Atsumi |
| 6,766,185 B2 | 7/2004 | Scott |
| 6,847,841 B1 | 1/2005 | El Hatw |
| 6,860,867 B2 | 3/2005 | Seward et al. |
| 6,869,430 B2 | 3/2005 | Balbierz et al. |
| 6,912,759 B2 | 7/2005 | Izadnegahdar et al. |
| 7,082,325 B2 | 7/2006 | Hashmishony et al. |
| 7,331,236 B2 | 2/2008 | Smith et al. |
| 7,611,482 B2 | 11/2009 | Naimark et al. |
| 7,809,425 B2 | 10/2010 | Hashimshony |
| 8,467,867 B2 | 6/2013 | Gianchandani et al. |
| 2001/0051774 A1 | 12/2001 | Littrup et al. |
| 2002/0026138 A1 | 2/2002 | Cowan, Jr. et al. |
| 2002/0026188 A1 | 2/2002 | Balbierz et al. |
| 2002/0115198 A1 | 8/2002 | Nerenberg et al. |
| 2003/0004411 A1* | 1/2003 | Govari ............... A61B 17/1114 600/424 |
| 2003/0100819 A1 | 5/2003 | Newman et al. |
| 2003/0018273 A1 | 6/2003 | Corl et al. |
| 2003/0199753 A1 | 10/2003 | Hibner et al. |
| 2004/0102733 A1 | 5/2004 | Naimark et al. |
| 2005/0261568 A1 | 11/2005 | Hular et al. |
| 2006/0004301 A1 | 1/2006 | Kasevich |
| 2007/0078484 A1 | 4/2007 | Talarico et al. |
| 2010/0081964 A1* | 4/2010 | Mark ............... A61B 10/0283 600/566 |
| 2012/0150061 A1 | 6/2012 | Yoo et al. |
| 2013/0158378 A1 | 6/2013 | Berger |
| 2014/0187870 A1 | 7/2014 | Weber |
| 2015/0351691 A1 | 12/2015 | Lieber et al. |
| 2016/0000514 A1* | 1/2016 | Ellman ............... A61B 18/1442 606/1 |
| 2016/0011216 A1* | 1/2016 | Feller ............... G01N 27/4145 422/69 |
| 2016/0157703 A1 | 6/2016 | Brooks et al. |
| 2018/0263540 A1 | 9/2018 | Zafar |

OTHER PUBLICATIONS

Ferris, Robert "How a Smart Scalpel Can 'Smell' Cancer During Surgery", Business Insider; retrieved from Internet: http://www.businessinsider.com/how-smart-scalpel-can-smell-cancer-2013-7; dated Jul. 24, 2013; 4 pgs.

Hsu, Jeremy "Smart Knife Detects Cancer in Seconds", retrieved from Internet: http://spectrum.ieee.org/tech-talk/biomedical/devices/smart-knife-detects-cancer-in-seconds; Posted Jul. 18, 2013; IEEE Spectrum; 2 pgs.

List of IBM Patents or Patent Applications Treated as Related; Date Filed: Nov. 22, 2019, 2 pages.

Wong, Sam "Intelligent Knife" tells surgeon if tissue is cancerous; retrieved from Internet: http://www3.imperial.ac.uk/newsandeventspg-grp/imperialcollege/newssummary/news_17-7-2013-17-17-32; dated Jul. 17, 2013; 3 pgs.

Zafar et al., "A Comparision Between Bipolar Transistor and Nanowire Field Effect Transistor Biosensors," Applied Physics Letters 106, 063701 (2015), AIP Publishing, 5 pgs.

Zafar et al., "Optimization of pH Sensing Using Silicon Nanowire Field Effect Transistors with HfO2 as the Sensing Surface," Nanotechnology 22 (2011) 405501, IOP Publishing, 7 pgs.

* cited by examiner

PH SENSITIVE SURGICAL TOOL

DOMESTIC PRIORITY

This application is a divisional of U.S. application Ser. No. 15/458,223, titled "PH Sensitive Surgical Tool" filed Mar. 14, 2017, the contents of which are incorporated by reference herein in its entirety.

BACKGROUND

The present invention relates in general to surgical instruments, and more specifically, to a pH sensitive surgical tool and related operations for real-time identification and removal of cancerous cells.

When a patient tissue is diagnosed as cancerous, patients can undergo surgical procedures to have the affected tissue removed. To prevent or minimize recurrence and renewed growth of a cancerous region, it is often necessary to remove all the cancerous cells. For the surgeon, it is not possible to distinguish every cancerous cell from every non-cancerous cell with the naked eye. Thus, other modes of detection are needed to determine whether all the cancerous cells have been excised in a surgical procedure. For instance, in a conventional surgical procedure, the surgeon removes a portion of tissue that potentially contains cancerous cells and sends the portion of tissue to a pathology laboratory to determine whether it is cancerous. If it is determined to be cancerous, the surgeon removes additional tissue in a subsequent surgical excision, sometimes in the same day. In some cases, a patient and surgical team can wait in the middle of surgery for pathology results to arrive before the surgical procedure can either continue or be concluded. Multiple iterations of the surgical procedure can be needed to remove affected tissue in its entirety.

A need exists to distinguishing non-cancerous tissue from cancerous tissue during a surgical procedure to improve patient comfort and to improve patient outcomes. A need also exists to identify cancerous cells with high spatial resolution during surgery.

SUMMARY

In accordance with one or more embodiments of the invention, a surgical apparatus for identification and removal of cancerous cells is provided. The apparatus includes a display including a pH measurement result. The apparatus also includes an apparatus tip including a reference electrode and a plurality of sensing surfaces, wherein each of the plurality of sensing surfaces is connected to a base of a bipolar junction transistor (BJT) device. The BJT device further includes a collector and an emitter. The apparatus also includes automation circuitry including a processing unit in communication with the apparatus tip and the display. The plurality of sensing surfaces includes a conducting material. These embodiments of the invention can advantageously allow real-time identification of cancerous tissue and thereby improve cancer treatment outcomes.

In accordance with one or more embodiments of the invention, a surgical apparatus for identification and removal of cancerous cells is provided. The apparatus includes a display including a pH measurement result. The apparatus also includes an apparatus tip including a reference electrode and a plurality of field effect transistor (FET) devices. The FET devices include a gate dielectric including a FET sensing surface, a source, a drain, and a substrate. The apparatus also includes automation circuitry including a processing unit in communication with the apparatus tip and the display. These embodiments of the invention can advantageously allow real-time identification of cancerous tissue and thereby improve cancer treatment outcomes.

In accordance with one or more embodiments of the invention, a surgical apparatus for identification and removal of cancerous cells includes a display including a pH measurement result, a tip including a reference electrode and a plurality of sensing surfaces, and optionally a scalpel blade. This embodiment of the invention can provide enhanced functionality to conventional surgical devices, for instance by allowing identification and removal of cancerous tissues with a single surgical instrument.

In accordance with another embodiment, a surgical apparatus for identification and removal of cancerous cells includes a display including a pH measurement result, a tip including a reference electrode and a plurality of sensing surfaces, and optionally a forceps. This embodiment of the invention can provide enhanced functionality to conventional surgical devices, for example by providing a pH sensing system on an instrument likely to be used in the removal of cancerous cells, reducing the need to exchange instruments during a surgical procedure.

In accordance with another embodiment, a surgical apparatus optionally includes a BJT-pH sensor array. A BJT-pH sensor array, for example, can advantageously provide a higher resolution sensing capacity than an apparatus in which a BJT-pH sensor array is not included by reducing the required surface area for functional components on the tip.

In accordance with a further embodiment, a method for identification and removal of cancerous tissue includes placing an apparatus for removal of cancerous cells in contact with an extracellular medium associated with a tissue of interest on a patient. The apparatus includes a display, an apparatus tip including a pH sensor, and automation circuitry including a processing unit in communication with the apparatus tip and the display. The method also includes measuring a local pH of the extracellular medium with the apparatus. The method also includes, based upon a determination that the local pH is acidic, excising the tissue of interest. Methods according to such embodiments of the invention can reduce the time and expense associated with cancerous tissue excision, for example by reducing the need for external laboratory testing and reducing the need for follow-on surgical procedures in cases where all tissue is not removed in a first surgery.

In accordance with another embodiment, a method for removal of cancerous tissue optionally includes measuring a collector current from a BJT collector. A collector current can, for example, lead to a computationally inexpensive pH calculation.

In accordance with another embodiment, a method for removal of cancerous tissue optionally includes measuring a drain current from a FET-pH sensor with a FET sensing surface applied to extracellular medium of a tissue of interest. A drain current measurement can, for example, also lead to a computationally inexpensive pH calculation.

In accordance with another embodiment, a method for removal of cancerous tissue optionally includes calibrating a pH sensor. Calibrating a pH sensor can advantageously improve the accuracy of a resultant pH measurement and, thus, provide increased confidence in removal of cancerous tissues.

BRIEF DESCRIPTION OF THE DRAWINGS

The subject matter of the present invention is particularly pointed out and distinctly claimed in the claims at the conclusion of the specification. The foregoing and other features and advantages of the one or more embodiments described herein are apparent from the following detailed description taken in conjunction with the accompanying drawings in which:

DETAILED DESCRIPTION

Systems and methodologies for identification and removal of cancerous tissue are provided. Removal of cancerous tissue frequently involves surgical extraction of the cancerous tissue. Conventionally, surgeons use visual and palpation methods to identify cancerous regions to be removed during surgery and to distinguish these regions from non-cancerous regions. While a patient is under anesthesia, surgeons can send out tissue samples to pathology labs to determine whether all cancerous cells of a region have been removed. Failure to remove all cancerous cells can lead to proliferation of remaining cancer cells and, thereby, re-occurrence of cancer.

In surgery, for instance, a surgeon can remove some tissue containing cancerous cells and send the tissue to a pathology lab. The patient can be sent home to heal with an uncertain surgical outcome, or in some cases wait with an open wound while a report is generated and returned to the clinician that details if and where any cancerous tissue remains. The clinician, after receiving the report can then return to the patient to remove more tissue, send newly excised tissue to the pathology lab, and repeat the remainder of the process. In some cases, several iterations could be conducted before all cancerous tissue is removed.

Conventional surgical methods of tumor removal are semi-quantitative with low spatial resolution. Moreover, conventional methods can lack a real-time identification of the boundary of a cancerous region. Accordingly, incomplete removal of a tumor can result, requiring a secondary surgery for treatment.

A need exists for surgical instruments and methods with high spatial resolution for cancerous cell removal. There is a need for improved instruments and methods for removal of cancerous tissues with real-time identification of cancerous skin cells.

Embodiments of the invention can overcome drawbacks associated with conventional methods. Tumor cells, such as medium-sized tumor cells, can be associated with an extracellular medium having a lower pH than the extracellular medium of healthy cells. Embodiments of the invention include a surgical tool with a solid-state label free pH sensor that can identify and define a tumor region, including during surgery. Embodiments of the invention can leverage the pH difference between cancerous and non-cancerous cells and, thereby, provide quantitative identification of cancerous skin cells in real-time. Thus, embodiments of the invention provide improved cancer treatment outcomes and a reduced incidence of secondary surgery.

Figure 1:
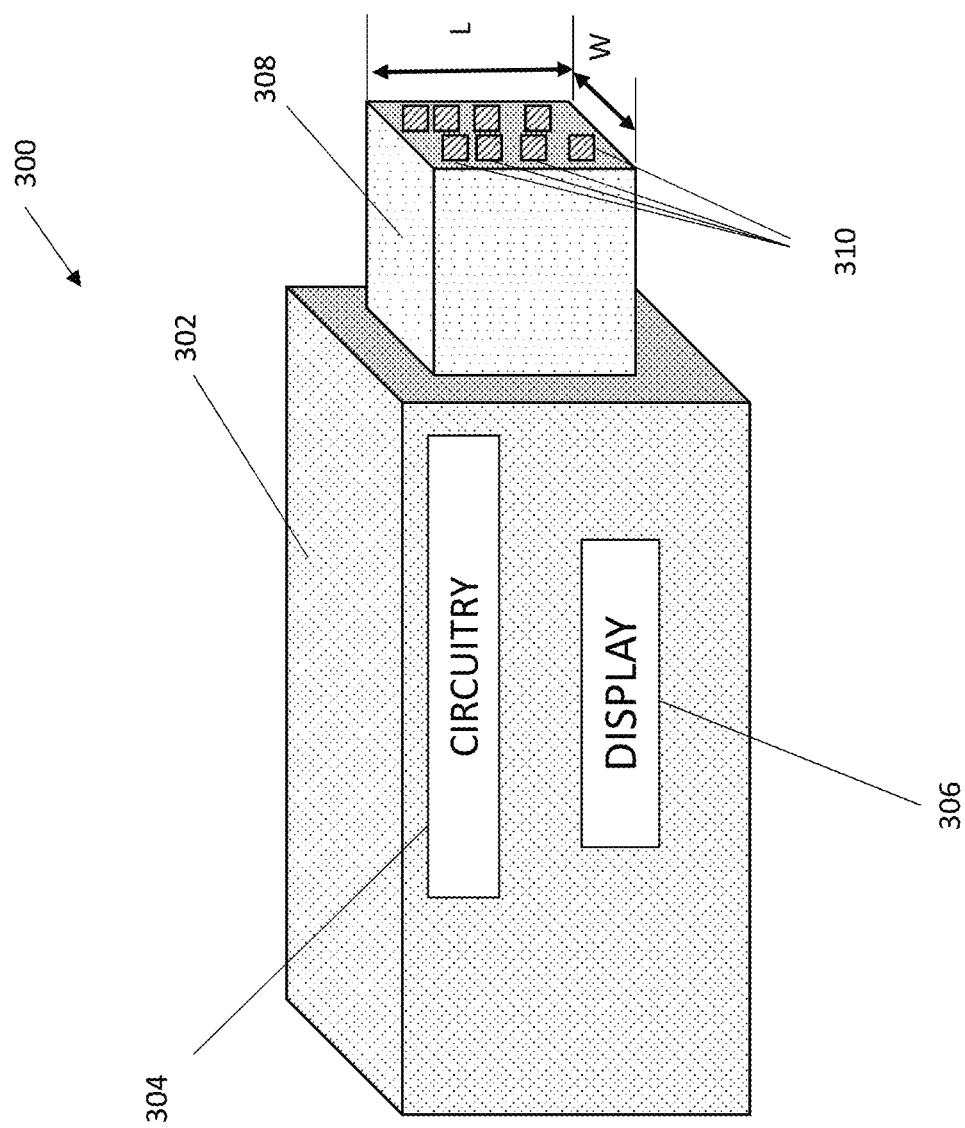
FIG. 1 depicts a surgical apparatus for identification of cancerous cells with high spatial resolution according to one or more embodiments of the present invention.

Turning now to a more detailed description of embodiments of the present invention, FIG. 1 depicts a surgical apparatus 300 for identification of cancerous cells with high spatial resolution according to one or more embodiments of the present invention. The apparatus 300 includes a handle 302 and an apparatus tip 308. The handle 302 and tip 308 can be any shape, such as rectangular, cubic, or cylindrical and can be the same size or differing sizes. The tip 308 has a length L and width W that can be of a size suitable for tumor removal applications. In some embodiments of the invention, the tip 308 has a width that is 2 to 10 mm, for instance 2 to 5 mm or 2 to 3 mm. In some embodiments of the invention, the tip 308 has a length that is 2 to 10 mm, for instance 2 to 5 mm or 2 to 3 mm. The tip 308 can include one or more pH sensors 310. In some embodiments of the invention, the tip 308 includes an array of pH sensors 310. The pH sensors 310 can be solid state device based sensors. In some embodiments of the invention, the pH sensors 310 are bipolar junction transistor (BJT) based pH sensors. In some embodiments of the invention, the pH sensors 310 are field effect transistor (FET) based pH sensors. In some embodiments of the invention, the pH sensors 310 include multiple sensors in a pH sensor array. The apparatus 300 can include automation circuitry 304. In some embodiments of the invention, the circuitry 304 serves to calibrate and measure pH in real-time. The circuitry 304 can include, for instance, data storage, processing unit(s), and wireless data transmission components. The circuitry 304 can communicate with the tip 308, including directly or indirectly with the pH sensors, and with a data display 306. In some embodiments of the invention, the data display 306 and automation circuitry 304 are included in the handle 302. For example, the automation circuitry 304 can be embedded within the handle 302 and the display unit 306 can be on the surface of the handle 302. In some embodiments of the invention, not shown in FIG. 1, the display 306 is external to the apparatus.

For example, the display 306 can be included within a smartphone, smart watch, laptop computer or PC. The data display 306 can display any data provided by the apparatus, including, but not limited to, a measured pH, position, battery life, memory capacity, and the like.

In some embodiments of the invention, the display includes a pH measurement result. The pH measurement result can include a quantitative or a qualitative indication of local pH. For example, a quantitative indication can include a numerical display of a pH value. A qualitative indication, for instance, can include a signal representing a pH above or below a threshold value. For example, a light of a particular color can signal a relatively high local pH, thus signaling to a surgeon the presence of cancerous tissue. The display can also include spatial information. For example, each sensing surface measures the local pH near its spatial vicinity. Thus, the area of the sensing surface is proportional to the spatial resolution of the sensor and the apparatus can, accordingly, provide quantitative spatial data to the display.

In some embodiments of the invention, the apparatus 300 is a stand-alone tool. In some embodiments of the invention, the apparatus 300 is included within or attached to another apparatus. For instance, the apparatus 300 can be attached to scalpel or forceps. The apparatus handle can be attached, for example, to the tip and to a scalpel or forceps, for instance, such that the handle is shared. In some embodiments of the invention, for example, a surgeon can both measure pH and perform a surgical function, such as tissue excision or manipulation, without the need to exchange tools. For instance, a scalpel can include a blade on one end and a tip on the opposite end or, a scalpel blade and tip on the same end of the apparatus such that pH measurement and excision of tissue involves minimal manipulation of the surgical apparatus.

The tip 308 of the apparatus 300, in operation, can be applied to a tissue sample to distinguish between cancerous (or tumor) regions and non-cancerous or (non-tumor) regions. Each BJT based pH sensor 310 of the tip can measure the collector current and, after calibration, the collected current can be associated with a local pH having a spatial resolution equal to the sensing surface dimensions. A relatively acidic local pH can be indicative of a cancerous region, whereas a pH of reduced relative acidity (a higher pH) can be associated with a non-cancerous region. By moving the tip 308 across a tissue sample, a surgeon can distinguish between areas of differing pH in real-time and, thereby, distinguish between cancerous and non-cancerous regions of tissue. Thus, in operation, an apparatus according to one or more embodiments of the invention can enable a surgeon to quantitatively distinguish between cancerous regions to be extracted and non-cancerous regions that do not require excision in real-time.

Figure 2:
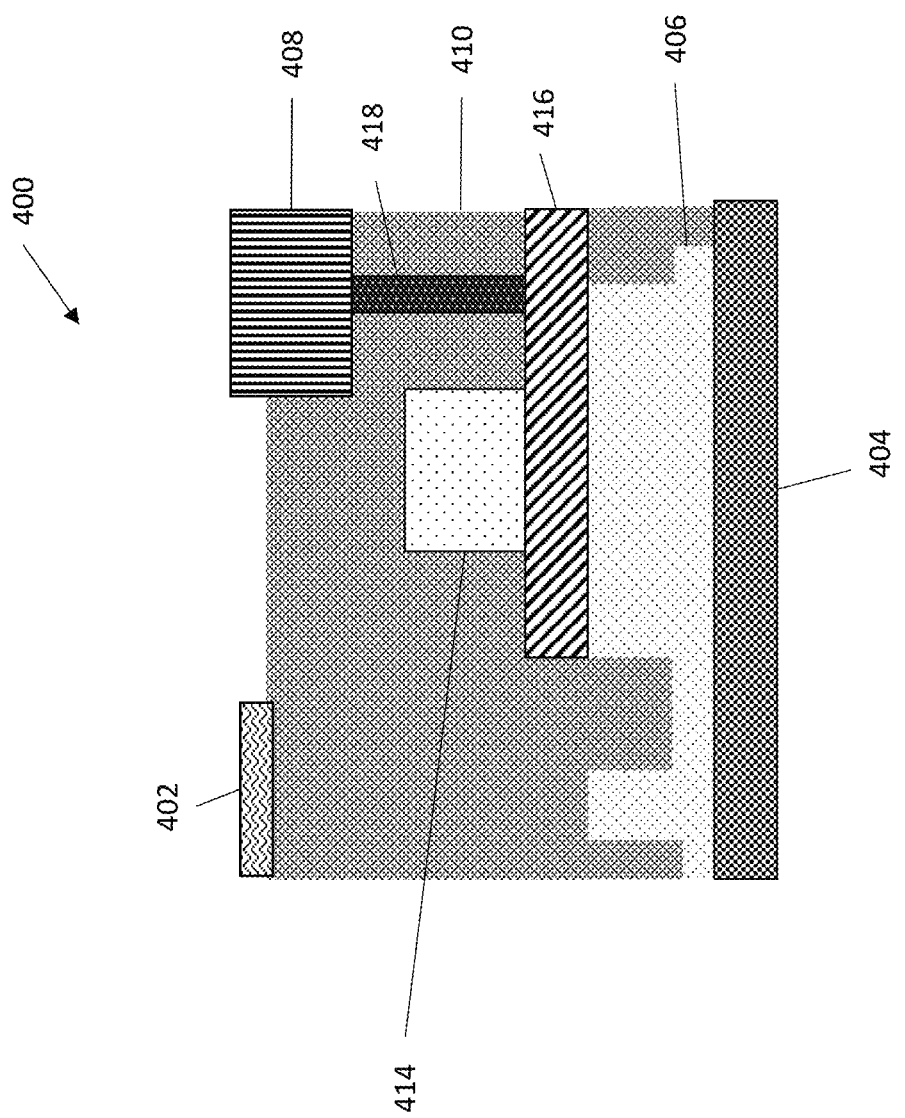
FIG. 2 depicts a cross-sectional side view of a BJT-pH sensor for use in the removal of cancerous cells according to one or more embodiments of the present invention.

FIG. 2 depicts a cross-sectional side view of a BJT-pH sensor 400 for use in the identification or detection of cancerous cells according to one or more embodiments of the invention of the present invention. BJT-pH sensor 400 includes a silicon substrate 404 and a collector 406 positioned on the silicon substrate 404. The BJT-pH sensor 400 also includes a base 416 formed on the collector 406. An emitter 414 can be formed on the base 416.

The BJT-pH sensor 400 can be an NPN type BJT or a PNP type BJT device. The selection of materials and dopant polarity can vary depending on whether the BJT-pH sensor is an NPN type or PNP type. For example, an NPN BJT can include a heavily doped n-type emitter 414, a p-type doped base 416, and a p-type doped collector 406. In some embodiments of the invention, the BJT-pH sensor 400 is a PNP type including, for instance, a heavily doped p-type emitter 414, an n-type doped base 416, and an n-type doped collector 406.

Silicon substrate 404 can include silicon or doped silicon. For example, the substrate 404 can include undoped silicon, p-type doped silicon or n-type doped silicon.

Collector 406 can include, for example, silicon, including doped or heavily doped silicon (i.e., more heavily doped than the substrate 404, which can be doped or undoped). The dopant polarity can be opposite to that of the substrate 404. For example, if the substrate 204 includes p-type doped silicon, the collector can include n-type heavily doped silicon. In some embodiments of the invention, collector 406 includes n-type heavily doped gallium arsenide (GaAs).

A base 416 can be formed on the collector 406. Base 416 can include, for instance, a doped silicon, such as silicon germanium (SiGe). In some embodiments of the invention, the silicon germanium is doped, or heavily doped (i.e., more heavily doped than the substrate 404). The dopant polarity can be opposite to that of the collector 406. For example, if the collector 206 includes n-type doped or heavily doped silicon, the base 416 can include p-type doped or heavily doped silicon germanium.

An emitter 414 can be formed on the base 416 and can include, for instance, silicon, polysilicon, or gallium arsenide. Emitter 414 can include polysilicon that is very heavily doped (i.e., doped more heavily than the collector 406 or the base 416).

As is further illustrated in FIG. 2, in one or more embodiments of the present invention BJT-pH sensor 400 includes a reference electrode 402 and a sensing surface 408. The reference electrode 402 can include, for example, a silver chloride reference electrode. The sensing surface 408 and reference electrode 402 can have surfaces externally accessible to the BJT-pH sensor such that they can be placed into contact with tissue and the extracellular medium associated with tissue. In some embodiments of the invention, the sensing surface(s) 408 are accessible to tissue when the BJT-pH sensor is included within a surgical apparatus for removal of cancerous cells according to one or more embodiments of the present invention. Base 416 can be electrically connected to the sensing surface 408 via a metal line 418. Metal line 418 can be a conductive metal wire, such as a tungsten wire.

The reference electrode 402 and sensing surface 408 are positioned on or embedded within an oxide layer 410 and each have an accessible surface for pH measurement. Oxide layer 410 can be composed of any oxide-based dielectric or insulating material that can be used for insulation in semiconductor devices, including but not limited to silicon dioxide, aluminum oxide, hafnium oxide, and combinations thereof.

The sensing surface 408 can have any shape. The sensing surface 408 can have a length or diameter of 5 to 15 micrometers (µm), for example from 5 to 10 µm or from 5 to 8 µm. In some embodiments of the invention, the sensing surface 408 has a length or diameter smaller than the diameter of a cell. For example, a cell can have a diameter of 10 µm and the sensing surface can have a diameter of 5 µm. The sensing surface 408 can be planar or have a three-dimensional shape. The area of the sensing surface can be directly related to the spatial resolution of the pH sensing apparatus.

In some embodiments of the invention, the sensing surface 408 includes conducting titanium nitride (TiN). The sensing surface 408 can be composed of any pH sensitive conducting material. In some embodiments of the invention, for example, sensing surface 408 includes a TiN film sputter deposited over a metal line 418. The sensing surface 408 can include, in some embodiments of the invention, platinum, ruthenium oxide, iridium oxide, conductive carbon, or combinations thereof.

In some embodiments of the present invention, a surgical apparatus includes a plurality of BJT-pH sensors, wherein each BJT-pH sensor includes one sensing surface. In some embodiments of the invention, a surgical apparatus includes a BJT-pH sensor array.

Figure 3:
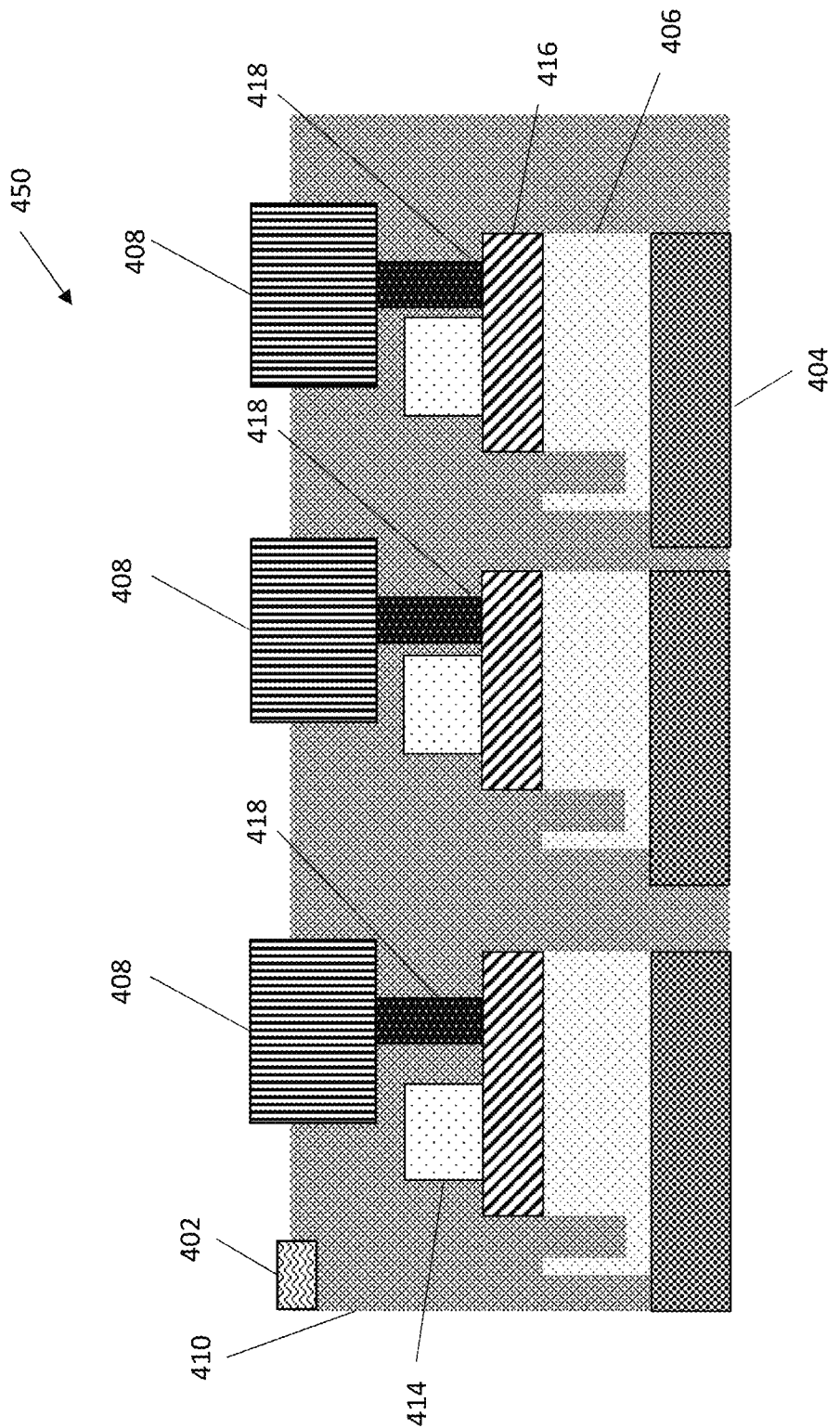
FIG. 3 depicts a cross-sectional side view of a portion of a pH sensor array for use in the removal of cancerous cells according to one or more embodiments of the present invention.

FIG. 3 depicts a cross-sectional side view of a portion of a pH sensor array 450 for use in the removal of cancerous cells according to one or more embodiments of the present invention. The array 450 includes a plurality of sensing surfaces 408. Each of the plurality of sensing surfaces can be connected to a metal line 418. The plurality of sensing surfaces 408 and metal lines 418 can be embedded within an oxide layer 410, such that the sensing surfaces 408 have a surface that can be accessible to a tissue sample. The array 450 includes a reference electrode 402. In some embodiments of the invention, the array 450 includes one reference electrode 402. In some embodiments of the invention, not shown in FIG. 3, the array 450 includes a plurality of reference electrodes 402.

The pH sensor array 450 can include other components, such as each of the components that are included in a BJT-pH sensor 400 according to one or more embodiments of the invention. For example, the plurality of sensing surfaces 408 can each be electrically connected to a base 406 via the plurality of metal lines 418. In some embodiments of the invention, each base 416 is positioned on a collector 406, which is positioned on a substrate 404. In some embodiments of the invention, a pH sensing array includes a plurality of emitters 414.

In operation, in some embodiments of the invention, a surgical apparatus for removal of cancerous cells is brought into contact with cells and the extracellular medium of a tissue of interest in an operation for removal of cancerous cells. The tissue of interest can include cancerous cells and non-cancerous cells in proximity to the cancerous cells.

Figure 4:
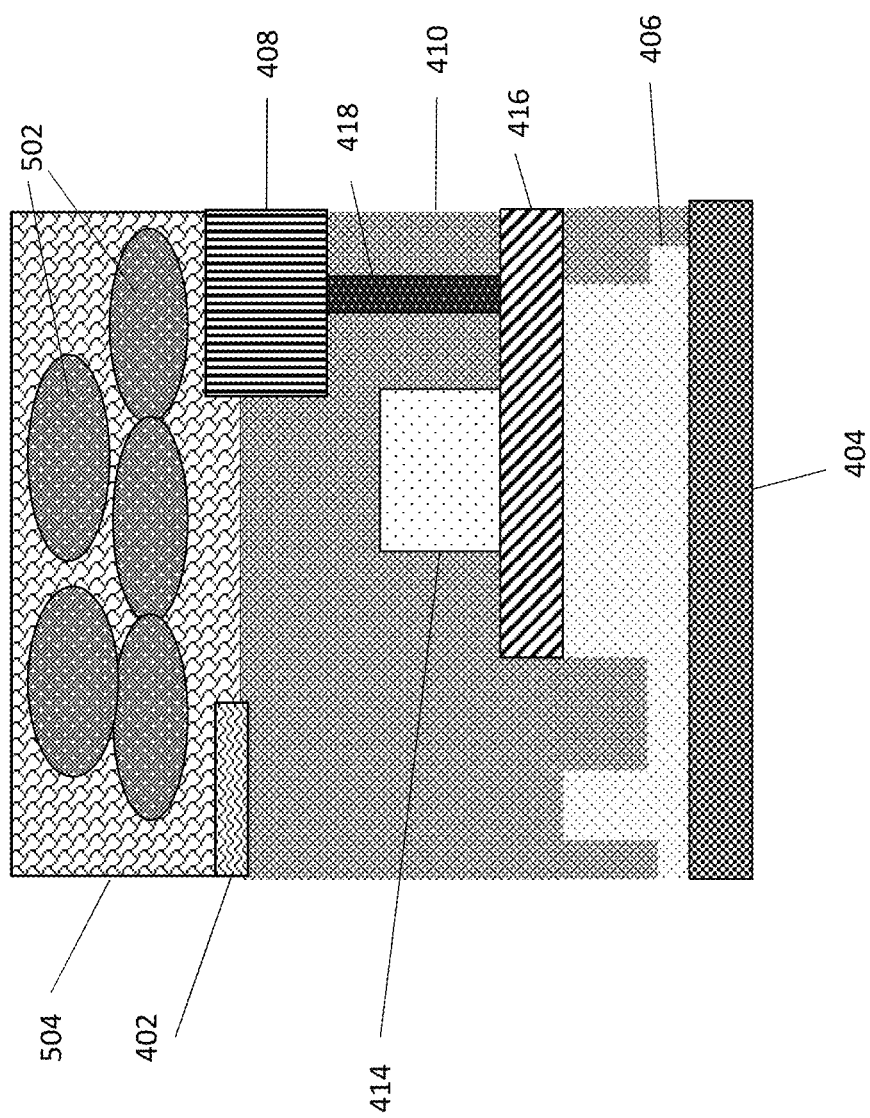
FIG. 4 depicts a cross-sectional side view of a portion of an apparatus for removal of cancerous skin cells in operation according to one or more embodiments of the present invention.

FIG. 4 depicts a cross-sectional side view of a portion of an apparatus for removal of cancerous skin cells in operation according to one or more embodiments of the present invention. As is shown, a sensing surface 408 is brought in contact with extracellular medium 504 surrounding a plurality of cells 502. Although FIG. 4 depicts a BJT-pH sensor, in some embodiments of the invention, a sensing surface is a surface of a FET-pH sensor. The cells 502 can be cells of tissue of interest and can include, for instance, cancerous and non-cancerous cells. The apparatus in operation can measure the local pH of the extracellular medium 504 to determine if the extracellular medium 504 is in a tumor environment or a non-tumor environment. An acidic pH can be indicative of a tumor environment, including an environment local to one or more cancerous cells.

In operation, a collector 406 and reference electrode 402 can be initially set at a voltage of zero. An emitter 414 can be held at a constant voltage and current is the sensing signal. In some embodiments of the invention, an apparatus includes an NPN BJT device and the emitter voltage is held at a constant voltage less than 0 Volts (V). In some embodiments of the invention, an apparatus includes an NPN BJT device and the emitter voltage is held at a constant voltage greater than 0 V.

In some embodiments of the invention, an apparatus is calibrated. For example, an apparatus including a BJT-pH sensor can be calibrated to determine sensing signal dependence on applied voltage and pH. After calibration, collector current can be measured at a fixed voltage and pH calculated therefrom.

Sensing of pH with a BJT-pH sensor can be performed in accordance known methods. For example, the principle of sensing can be determined by measuring the sensing current at the device collector, following the Ebers-Moll equation as follows:

$$I_C = I_o \exp\{q(V_B + \psi_s - I_B R - V_E / kT\}.$$

wherein $I_C$ is the collector current $I_o$ is a constant dependent upon device parameters, q is the electronic charge, $V_B$ is the base voltage applied at the reference electrode, $\psi_s$ is the sensing surface potential, $I_B$ is the base current flowing through the solution, R is the resistance of the solution, $V_E$ is the emitter voltage, k is the Boltzmann constant, and T is the device temperature. As is known and described elsewhere, $I_B R$ can be treated as negligible. Thus, the system can be calibrated with known pH buffer solutions and measuring sensing current $I_C$ as a function of applied voltage $V_{BE} = (V_B - V_E)$.

Figure 5:
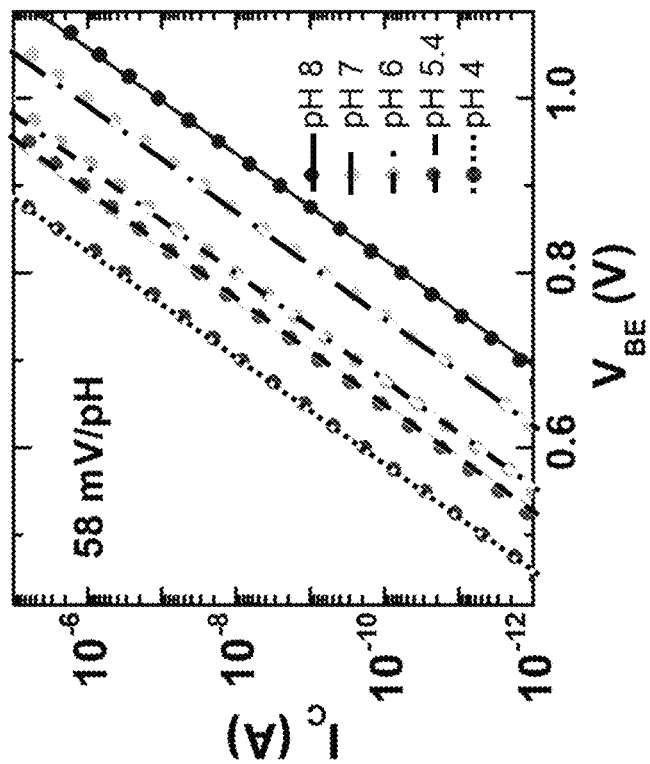
FIG. 5 is a chart depicting collector current versus the difference between the voltage applied at the base and the voltage applied at the emitter of an exemplary BJT-pH sensor for use in embodiments of the present invention.

FIG. 5 is a chart depicting collector current versus the difference between the voltage applied at the base and the voltage applied at the emitter of an exemplary BJT-pH sensor for use in embodiments of the present invention. FIG. 5 demonstrates sensing signal ($I_C$) dependence on applied voltage and pH. Buffered solutions having known pH values of 4, 5.4, 6, 7, and 8 can each be applied to a BJT-pH sensor, such as a BJT-pH sensor of a tip of an apparatus for use in embodiments of the present invention. $I_C$ can be measured and plotted against the applied voltage $V_{BE}$. FIG. 5 illustrates a BJT pH sensor with a voltage per pH unit of 58 millivolts (mV).

In some embodiments of the invention, calibration results are used to determine a local pH of a tissue of interest. For example, a fixed applied voltage can be applied to a system having one or more BJT-pH sensors and a sensing signal ($I_C$) can be measured in real time. From the sensing signal, pH can readily be calculated with the calibration results.

Figure 6:
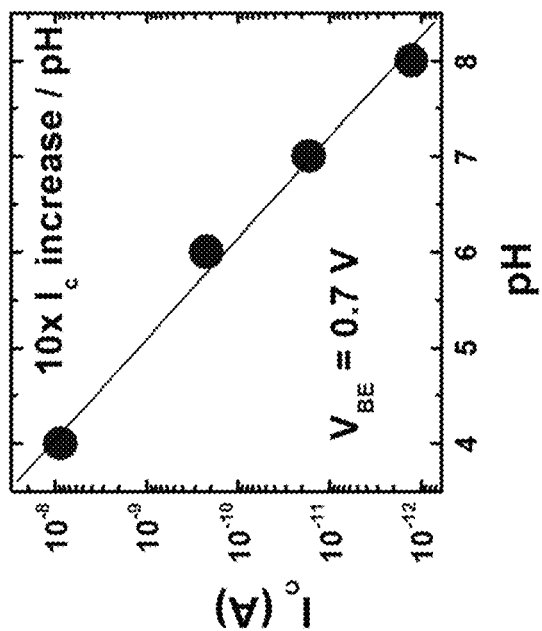
FIG. 6 is a chart depicting collector current at a fixed voltage of 0.7 V versus pH for the exemplary BJT-pH sensor represented in FIG. 5.

FIG. 6 is a chart depicting collector current at a fixed voltage of 0.7 V versus pH for the exemplary BJT-pH sensor represented in FIG. 5. Application of a fixed voltage and measurement of sensing signal can provide a pH measurement in real time.

As is illustrated in FIGS. 5 and 6, the sensing signal of embodiments of the invention of the invention can increase up to ten units per pH unit, resulting in a system with high sensitivity. Moreover, sensitivity in embodiments of the invention is independent of salt concentrations.

Figure 7:
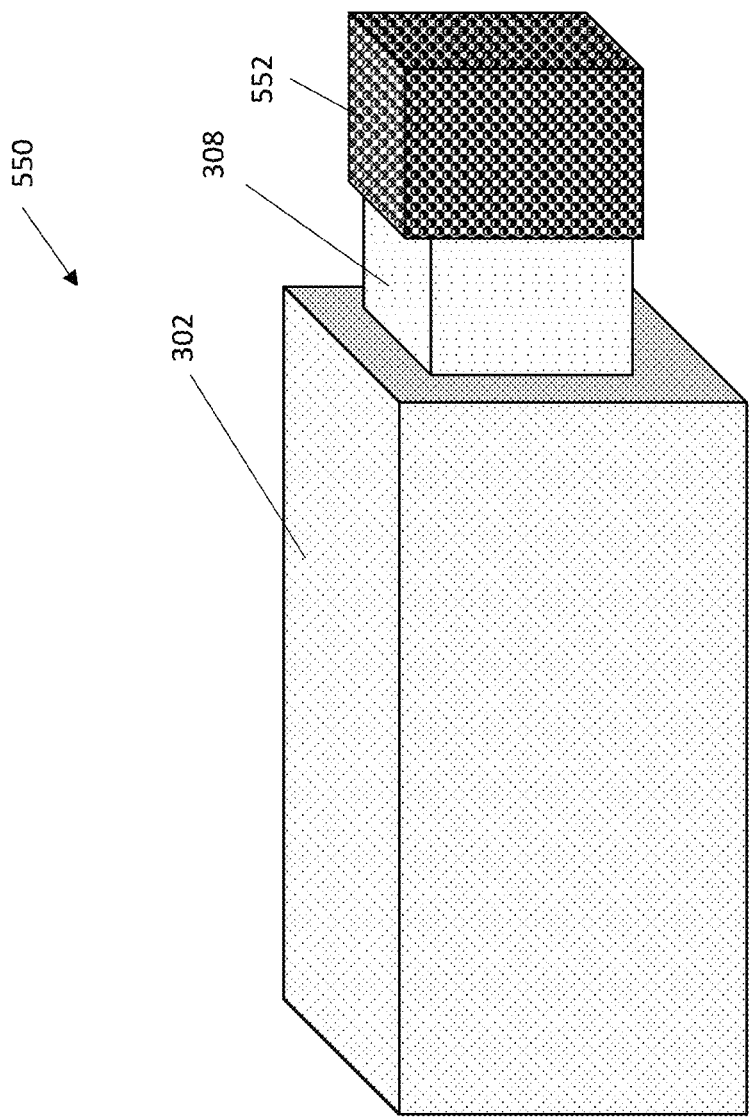
FIG. 7 depicts a storage system for an apparatus for removal of cancerous skin cells according to one or more embodiments of the present invention.

FIG. 7 depicts a storage system 550 for an apparatus for removal of cancerous skin cells according to one or more embodiments of the present invention. The storage system 550 includes a cap 552 covering a portion of the tip 308. In some embodiments of the invention, the cap 552 covers pH sensors of the system (not shown in FIG. 7). In some embodiments of the invention, the cap 552 holds an aqueous storage solution, such as a saline solution, or a buffered pH-saline solution (not shown), in contact with the pH sensors (not shown). Providing a cap 552 with an aqueous solution such as a pH buffer including 1-5 millimolar (mM) NaCl can advantageously protect or preserve the pH sensors of embodiments of the present invention. In some embodiments of the invention, the storage system 550 results in minimum signal drifts or can have improved settling times over the settling times of dry sensing surfaces, which can be on the order of several minutes.

Figure 8:
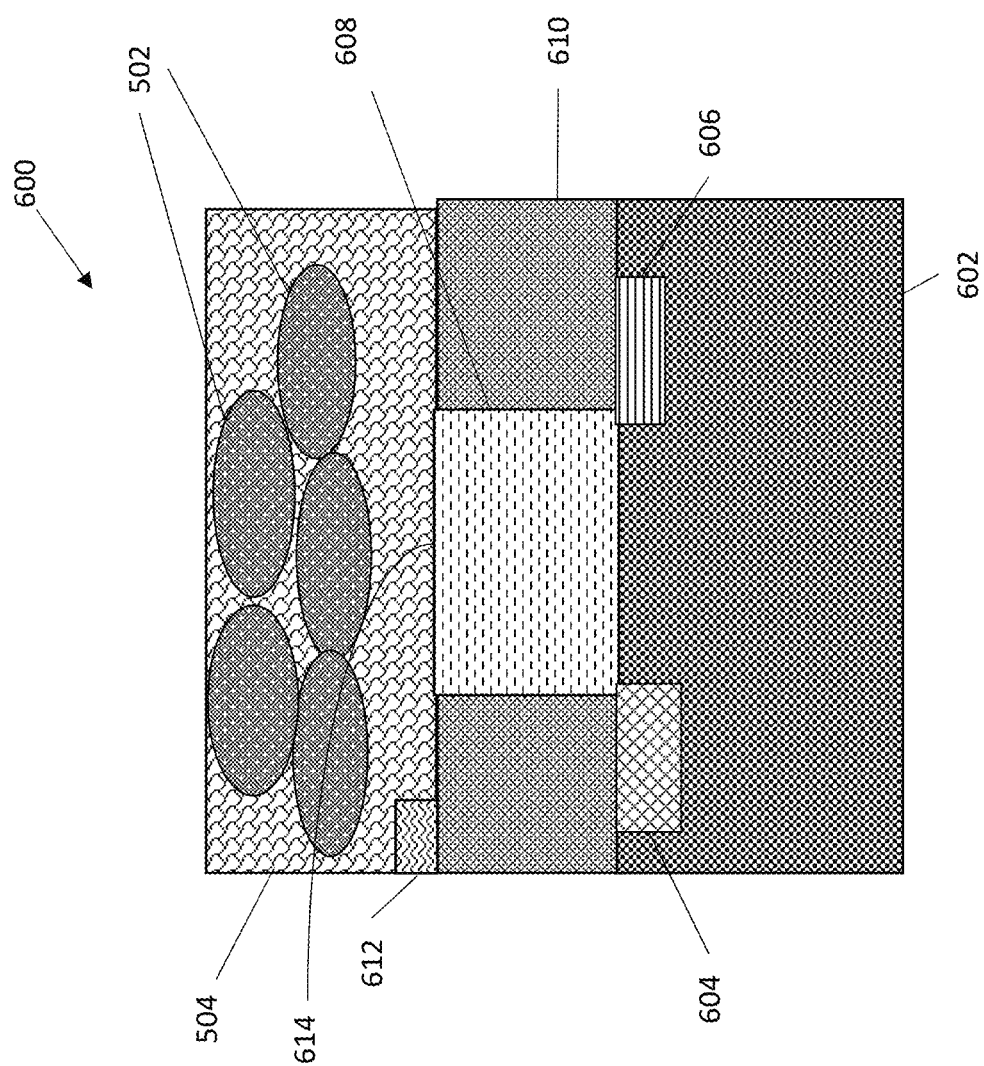
FIG. 8 depicts a cross-sectional side view of a FET-pH sensor for use in the removal of cancerous skin cells according to one or more embodiments of the present invention.

FIG. 8 depicts a cross-sectional side view of a FET-pH sensor 600 for use in the removal of cancerous skin cells according to one or more embodiments of the present invention. The FET-pH sensor 600 includes a FET silicon substrate 602 and a source 604 and drain 606. FET Silicon substrate 602 can include silicon or doped silicon, for example the substrate 602 can include a silicon-on-insulator wafer (SOI) with lightly doped p-type silicon. The FET-pH sensor 600 can include an oxide layer 610. The FET-pH sensor 600 includes a gate dielectric 608 atop the FET silicon substrate 602. The FET-pH sensor includes a FET reference electrode 612. The FET reference electrode 612 can include, for example, silver chloride. The gate dielectric 608 and FET reference electrode 612 can be embedded within or on top of the oxide layer 610.

Each of the gate dielectric 608 and the FET reference electrode 612 can have surfaces externally accessible to the FET-pH sensor such that they can be placed into contact with tissue and the extracellular medium associated with tissue and extracellular medium associated with tissue. In some embodiments of the invention, the externally accessible surface(s) of the gate dielectric 608 and the FET reference electrode 612 are accessible to tissue when the FET-pH sensor is included within a surgical apparatus for removal of cancerous cells according to one or more embodiments of the present invention.

Source 604, and drain 606 can be composed of materials conventionally used for such components in FET-devices and can be formed by conventional methods. Source 604 and drain 606 are formed on opposing sides of the gate dielectric 608. For example, source 604 and drain 606 can be formed with an epitaxial growth process to deposit a crystalline layer onto the FET substrate 602. The epitaxial silicon, silicon germanium, and/or carbon doped silicon (Si:C) can be doped during deposition by adding a dopant or impurity to form a silicide. The epitaxial source/drain can be doped with an n-type dopant or a p-type dopant, which depends on the type of transistor. In some embodiments of the invention, the source 604 and drain 606 include heavily boron doped source and drain regions. Alternatively, the source/drain 604/606 can be formed by incorporating dopants into the substrate 602.

FET Oxide layer 610 can be formed over the source 604 and drain 606 and around the gate dielectric 608. The FET oxide layer 610 can include, for example, a low-k dielectric oxide. In some embodiments of the invention, FET oxide layer 610 includes tetra-ethyl orthosilicate (TEOS) oxide.

Gate dielectric 608 can include any insulating material that is sensitive to pH. In some embodiments of the invention, gate dielectric includes hafnium dioxide ($HfO_2$), aluminum oxide ($Al_2O_3$), vanadium oxide ($V_2O_5$), titanium oxide ($TiO_2$), tungsten oxides, or combinations thereof. In some embodiments of the invention, in operation, gate dielectric 608 includes a FET sensing surface 614 (the external surface of the gate dielectric) for determining local pH of tissue. In some embodiments of the invention, gate dielectric 608 is composed of $HfO_2$. In operation, extracellular fluid 504 forms the gate of the FET device. The extracellular fluid 504 can be in contact with a plurality of cells 502.

In some embodiments of the invention, FET-pH sensors do not include a metal gate. In some embodiments of the invention, the gate dielectric forms the FET sensing surface in contact with the extracellular medium. In operation, the FET-pH sensor reference electrode is also in contact with the extracellular medium in some embodiments of the invention.

The FET sensing 614 surface can have any shape. The sensing surface can have a length or diameter of 5 to 15 micrometers (μm), for example from 5 to 10 μm or from 5 to 8 μm. In some embodiments of the invention, the FET sensing surface has a length or diameter smaller than the diameter of a cell. For example, a cell can have a diameter of 10 μm and the FET sensing surface 614 can have a diameter of 5 μm.

Sensing of pH with a FET-pH sensor can be performed in accordance with known methods. In operation, according to some embodiments of the invention, the sensing signal is a drain current ID. Measurements can be made by setting the reference electrode voltage equal to a gate voltage, setting the drain to a small voltage (e.g., |30 mV|) and setting the source voltage to 0 V. The silicon substrate can be set to 0 V at the back side. A device including a FET-pH sensor can be applied to a solution or extracellular medium such that a sensing surface and reference electrode are exposed to the fluid. Measurements of drain current can be taken and used to determine local pH.

In some embodiments of the invention, an apparatus including a FET-pH sensor can be calibrated to determine sensing signal dependence on voltage and pH. After calibration, drain current can be measured at a fixed voltage and pH calculated therefrom.

Figure 9:
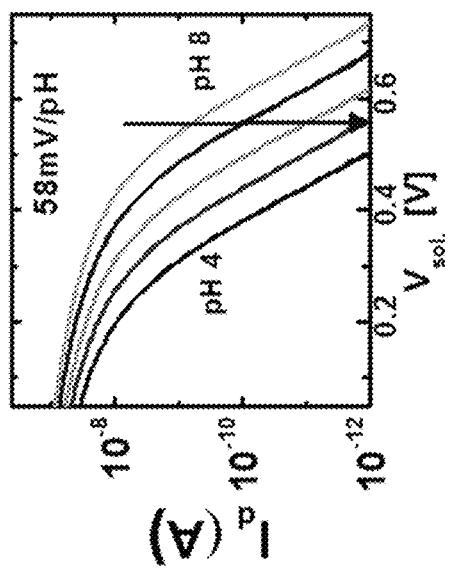
FIG. 9 is a chart depicting drain current versus gate voltage of an exemplary FET-pH sensor for use in embodiments of the present invention.

FIG. 9 is a chart depicting drain current ($I_D$) versus gate voltage $V_{SOL}$ of an exemplary FET-pH sensor for use in embodiments of the present invention. FIG. 5 demonstrates sensing signal ($I_D$) dependence on gate voltage and pH. Buffered solutions, such as phosphate buffer of 100 mM concentration, having known pH values of 4, 5.4, 6, 7, and 8 can each be applied to a FET-pH sensor, such as a FET-pH sensor of a tip of an apparatus for use in embodiments of the present invention. $I_D$ can be measured and plotted against the gate voltage $V_{SOL}$. FIG. 5 illustrates a FET-pH sensor with a voltage per pH unit of 58 mV.

In some embodiments of the invention, calibration results are used to determine a local pH of a tissue of interest. For example, a fixed applied voltage can be applied to a system having one or more FET-pH sensors and a sensing signal ($I_D$) can be measured in real time. From the sensing signal, pH can readily be calculated with the calibration results.

Figure 10:
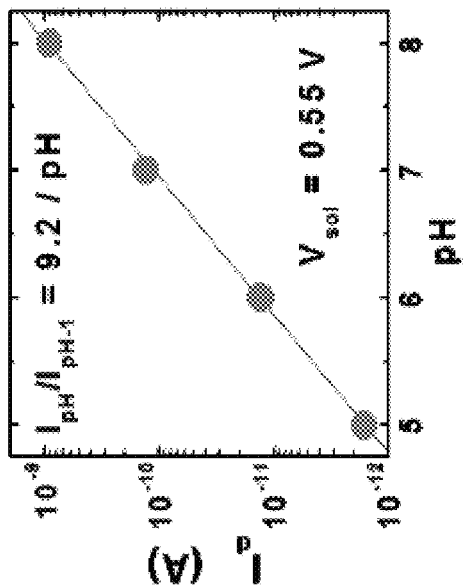
FIG. 10 is a chart depicting drain current at a fixed gate voltage of 0.55 V versus pH for the exemplary FET-pH sensor represented in FIG. 9.

FIG. 10 is a chart depicting drain current at a fixed voltage of 0.0.55 V versus pH for the exemplary FET-pH sensor represented in FIG. 9. Application of a fixed voltage and measurement of sensing signal can provide a pH measurement in real time.

As is illustrated in FIGS. 9 and 10, the sensing signal of embodiments of the invention can result in a system with high sensitivity. Moreover, some embodiments of the invention including FET-pH sensors are sensitive to $H^+$ only. For example, FET-pH sensors including $HfO_2$ can be sensitive to $H^+$ only. In some embodiments, desirably, systems and apparatus use a low sensing voltage, such as a voltage of less than 1 V.

Embodiments of the present invention can provide a number of technical features and benefits. For example, embodiments of the present invention can provide real-time pH measurements with high spatial resolution for detection and identification of cancerous cells during surgery. Such measurements can improve surgical outcomes and patient comfort and reduce medical costs associated with cancer treatment, for example, by reducing the need for repeated surgical procedures, reducing the need for repeated laboratory testing of tissue samples, and by reducing the time expended by medical personnel during surgical excision.

Figure 11:
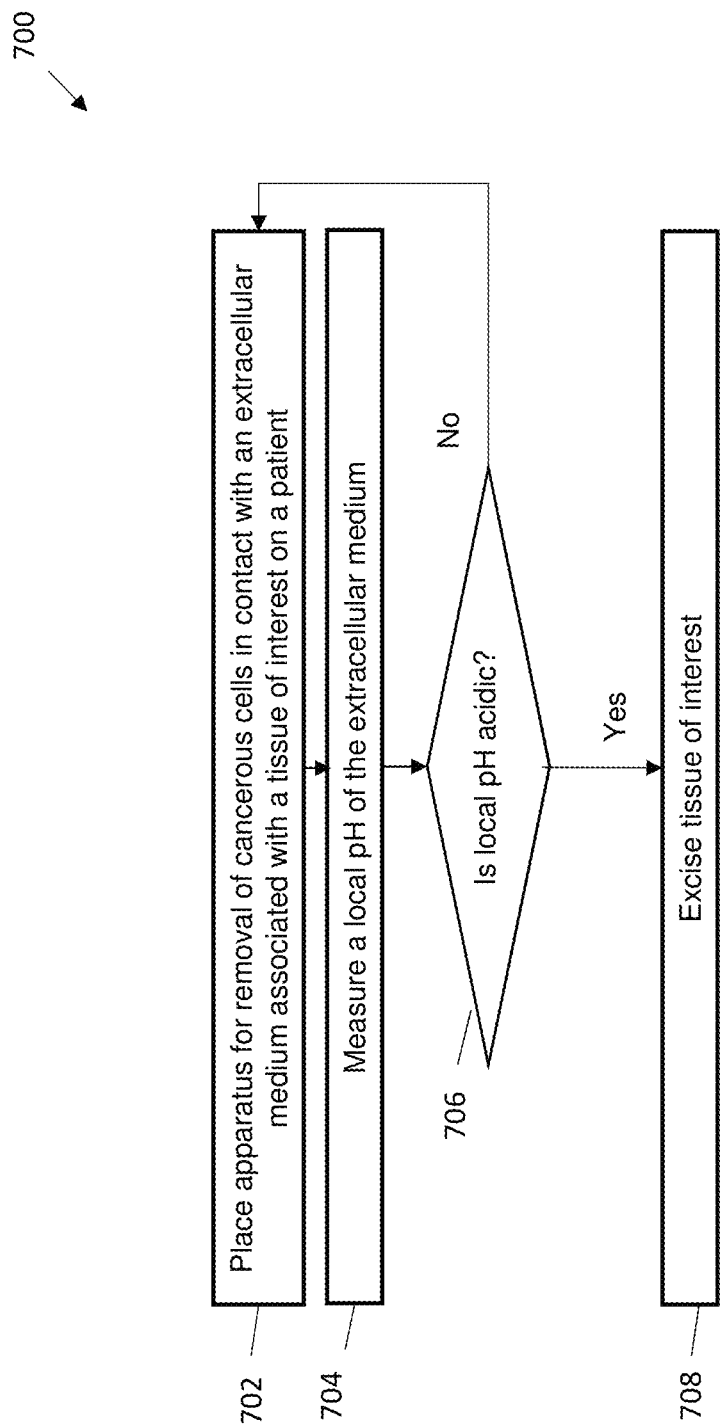
FIG. 11 is a flow diagram of a method for removing cancerous tissue according to one or more embodiments of the present invention.

FIG. 11 is a flow diagram of a method for removing cancerous tissue 700 according to one or more embodiments of the present invention. As is shown at block 702, the method includes placing an apparatus for removal of cancerous cells in contact with an extracellular medium associated with a tissue of interest on a patient. The tissue of interest can be, for example, skin tissue. The method 700 includes, as shown at block 704, measuring a local pH of the extracellular medium. The method 700 includes determining whether the local pH is acidic, as is shown at decision block 706. Responsive to a determination that the local pH is not acidic, the method 700 can return to block 702. Responsive to a determination that the local pH is acidic, the method 700 includes excising the tissue of interest, as shown at block 708.

Figure 12:
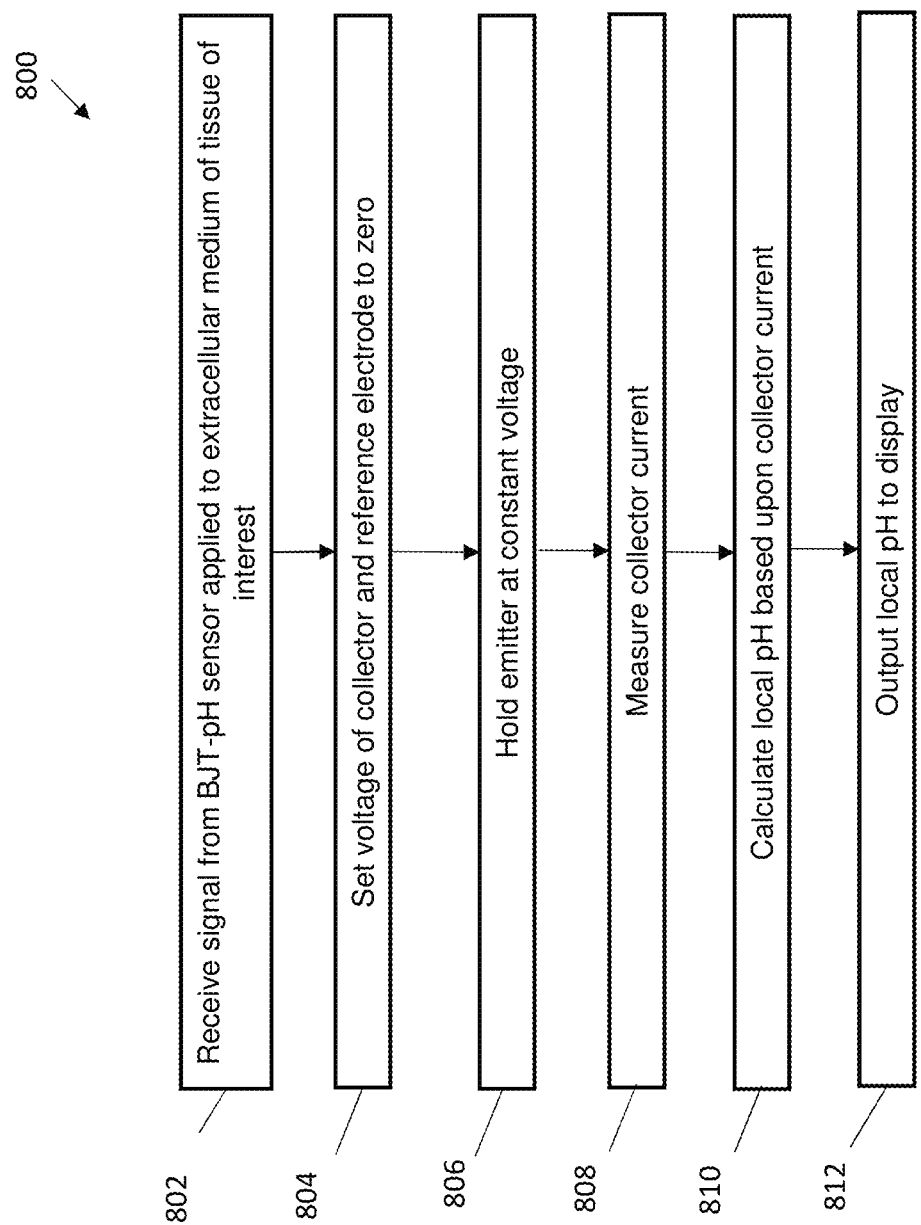
FIG. 12 is a flow diagram of a method for identifying cancerous tissue with a surgical apparatus in accordance with one or more embodiments of the present invention.

FIG. 12 is a flow diagram of a method for identifying cancerous tissue with a surgical apparatus 800 in accordance with one or more embodiments of the present invention. The method 800 includes, as is shown at block 802, receiving a signal from a BJT-pH sensor applied to extracellular medium of a tissue of interest. The method 800 also includes, as shown at block 804, setting the voltage of a collector and reference electrode to zero. The method 800 also includes, as shown at block 806, holding the emitter of the BJT-pH sensor at a constant voltage. As shown at block 808, the method 800 includes measuring collector current. The method 800 also includes, as shown at block 810, calculating a local pH based upon collector current. As shown at block 812, the method 800 includes outputting the local pH to a display.

Figure 13:
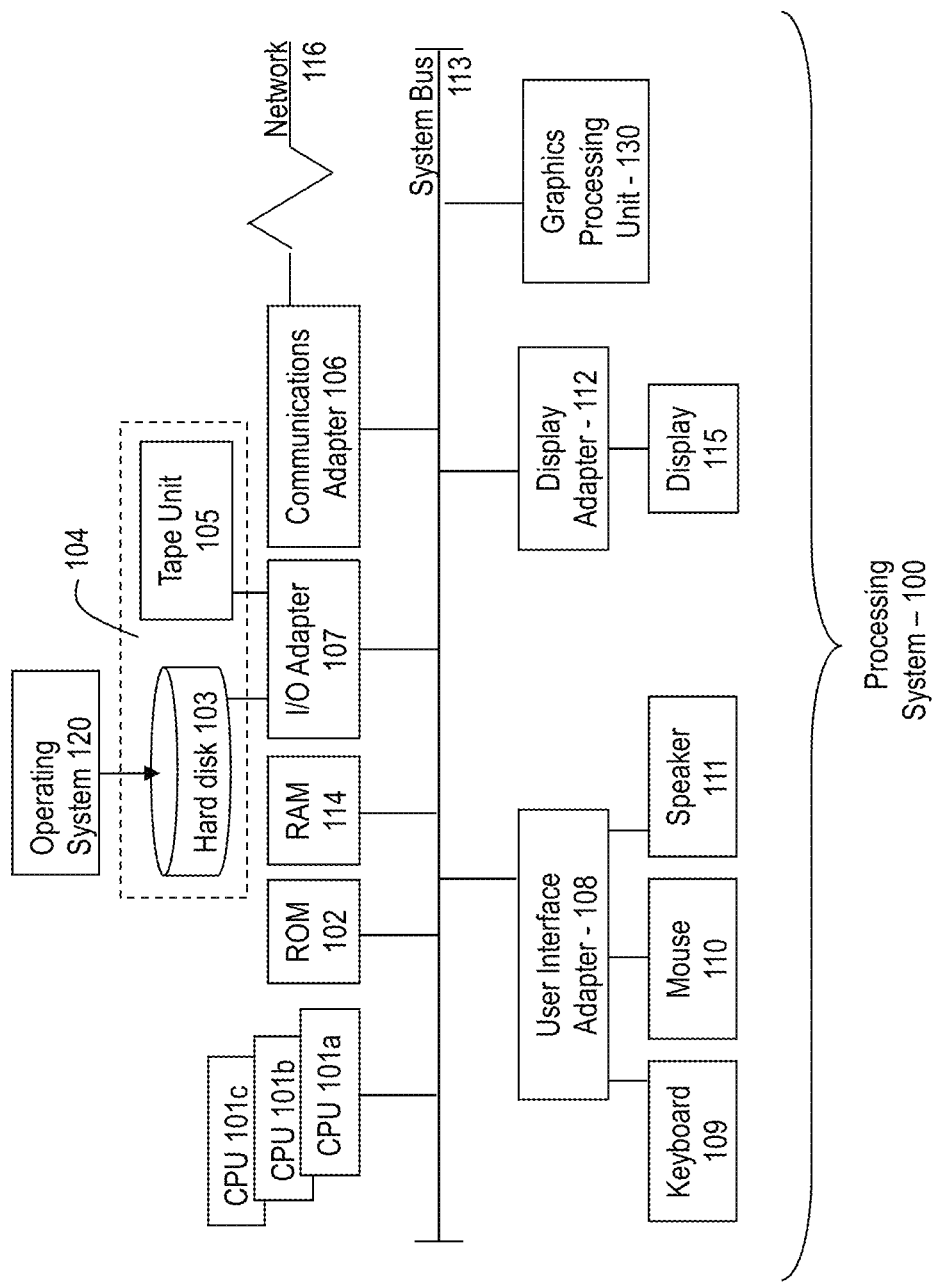
FIG. 13 is a block diagram illustrating one example of a processing system in accordance with an exemplary embodiment.

Referring to FIG. 13, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 13 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

In exemplary embodiments of the invention, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 13, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 13.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

The present invention can be a system, a method, and/or a computer program product at any possible technical detail level of integration. The computer program product can include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A surgical apparatus for identification of cancerous cells, the apparatus comprising:
   a display;
   an apparatus tip comprising an array of bipolar junction transistor-pH (BJT-pH) sensors, the apparatus tip further comprising a length of 2 to 10 mm and a width of 2 to 10 mm, wherein each BJT-pH sensor comprises:
      a sensing surface positioned on a surface of an oxide layer, the sensing surface having a diameter of 5 to 15 micrometers;
      a reference electrode positioned on the surface of the oxide layer;
      a collector; and
      an emitter; and
   automation circuitry comprising a processing unit in communication with the apparatus tip and the display; wherein the sensing surfaces comprise a conducting material.

2. The surgical apparatus of claim 1 further comprising a scalpel blade.

3. The surgical apparatus of claim 2 further comprising an apparatus handle, wherein the apparatus handle is physically connected to the apparatus tip and the scalpel blade.

4. The surgical apparatus of claim 1 further comprising a forceps.

5. The surgical apparatus of claim 1, wherein the display is positioned on an apparatus handle.

6. The surgical apparatus of claim 1, comprising a pH sensor array.

7. The surgical apparatus of claim 1 further comprising a cap and a storage solution, wherein the cap covers the sensing surfaces and holds the storage solution in proximity to the sensing surfaces.

8. The surgical apparatus of claim 1, wherein the sensing surfaces comprise TiN.

* * * * *